(12) United States Patent
Larsen et al.

(10) Patent No.: US 12,735,736 B2
(45) Date of Patent: Sep. 15, 2026

(54) MARINE DNA POLYMERASE I

(71) Applicant: Universitetet I Tromsø—Norges Arktiske Universitet, Langnes (NO)

(72) Inventors: Atle Noralf Larsen, Kvaløya (NO); Yvonne Piotrowski, Tromsø (NO)

(73) Assignee: Universitetet I Tromso—Norges Arktiske Universitet, Langnes (NO)

(*) Notice: Subject to any disclaimer, the term of this patent is extended or adjusted under 35 U.S.C. 154(b) by 948 days.

(21) Appl. No.: 17/765,572

(22) PCT Filed: Oct. 1, 2020

(86) PCT No.: PCT/EP2020/077534

§ 371 (c)(1),
(2) Date: Mar. 31, 2022

(87) PCT Pub. No.: WO2021/064108

PCT Pub. Date: Apr. 8, 2021

(65) Prior Publication Data

US 2023/0220449 A1 Jul. 13, 2023

(30) Foreign Application Priority Data

Oct. 1, 2019 (EP) .................................... 19200782

(51) Int. Cl.

| | |
|---|---|
| ***C12P 21/06*** | (2006.01) |
| ***C12N 9/12*** | (2006.01) |
| ***C12Q 1/48*** | (2006.01) |
| ***C12Q 1/6818*** | (2018.01) |

(52) U.S. Cl.

CPC ......... *C12Q 1/6818* (2013.01); *C12N 9/1252* (2013.01); *C12Q 1/48* (2013.01); *C12Y 207/07007* (2013.01)

(58) Field of Classification Search

USPC .................................................. 530/300, 350

See application file for complete search history.

(56) References Cited

U.S. PATENT DOCUMENTS

2013/0323795 A1* 12/2013 Duthie ................ C12Q 1/6844 435/194

FOREIGN PATENT DOCUMENTS

| | | | |
|---|---|---|---|
| EP | 1915446 | B1 | 4/2008 |
| EP | 1929012 | B1 | 6/2008 |
| WO | WO 2006/030455 | A1 | 3/2006 |
| WO | 2016026574 | A1 | 2/2016 |
| WO | 2017162765 | A1 | 9/2017 |

OTHER PUBLICATIONS

Tully et al., DNA polymerase I nucleotide sequence submitted to the EMBL/GenBank/DDBJ databases on Aug. 2017.*

(Continued)

*Primary Examiner* — Frank W Lu

(74) *Attorney, Agent, or Firm* — Karen A. LeCuyer; DeWitt LLP

(57) ABSTRACT

The present invention relates to DNA polymerases. In particular, the present invention relates to heat labile DNA polymerases of marine origin, having high polymerase activity, strand displacement activity and 3-5' exonuclease activity. Furthermore, the present invention provides heat labile DNA polymerases substantially without strand-displacement activity.

8 Claims, 6 Drawing Sheets

Specification includes a Sequence Listing.

(56) References Cited

OTHER PUBLICATIONS

Piotrowski et al., Characterization and engineering of a DNA polymerase reveals a single amino-acid substitution in the fingers subdomain to increase strand-displacement activity of A-family prokaryotic DNA polymerases. BMC Molecular and Cell Biology, 20, 31, 2019.*

Notification of the First Office Action dated Mar. 13, 2024, for Chinese Application No. 2020800691450, with English translation.

Phi29 DNA Polymerase. Thermoscientific User Guide. Aug. 2, 2019.

GenBank: PHR92264.1. MAG: DNA polymerase I. Oct. 26, 2017.

Notification of Reasons for Rejection for JP Application No. 2022-520140 dated Jul. 9, 2024, with English Translation.

A0A2G2J1S6 •A0A2G2J1S6_9PROT, UniProt, 2018, pp. 1-4, https://www.uniprot.org/uniprotkb/A0A2G2J1S6/entry.

Instruction Manual phi29 DNA Polymerase Set, Kanto Chemical Co., Ltd., 2014, pp. 1-2.

A0A2D8ZQ76 • A0A2D8ZQ76_9PROT, UniProt, 2018, pp. 1-4, https://www.uniprot.org/uniprotkb/A0A2D8ZQ76/entry.

A0A2D7XRX0• A0A2D7XRX0_9PROT, UniProt, 2018, pp. 1-4, https://www.uniprot.org/uniprotkb/A0A2D7XRX0/entry.

Anonymous; "Polymerases from NEB"; [Online] retrieved from http://neb.com/nebecomm/tech_reference/polymerase/polymerases_from_neb.asp on Jun. 1, 2012; 3 pages.

Database geneseq [Online] Apr. 25, 2018 (Apr. 25, 2018), "DNA polymerase I"; retrieved from EBI Accession No. UNIPROT:A0A2D7XRX0.

Database geneseq [Online] Jan. 31, 2018 (Jan. 31, 2018), "DNA polymerase I"; retrieved from EBI Accession No. UNIPROT:A0A2D8ZQ76.

Database geneseq [Online] Jan. 31, 2018 (Jan. 31, 2018), "DNA polymerase I"; retrieved from EBI Accession No. UNIPROT:A0A2G2J1S6.

European Search Report for European Application 19200782.1 [PCT/EP2020/077534] dated Jan. 17, 2020; 10 pages.

Gibson, D. et al.; "Enzymatic assembly of DNA molecules up to several hundred kilobases"; Nature Methods, vol. 6, Issue No. 5; 2009; pp. 343-345.

International Search Report and Written Opinion for International Application PCT/EP2020/077534; International Filing Date: Oct. 1, 2020; Date of Mailing: Dec. 2, 2020; 17 pages.

Li, et al.; "SLIC: a method for sequence and ligation independent cloning"; Gene Synthesis, vol. 852; 2012; pp. 51-59.

Mcwilliam, et al.; "Analysis Tool Web Services from the EMBL-EBI"; Nucleic Acids Research, vol. 41; 2013; pp. W597-W600.

Notomi, T. et al.; "Loop-mediated isothermal amplification of DNA"; Nucleic Acids Research, vol. 28, Issue No. 12, Article e63; 2000; 7 pages.

Piotrowski, Y. et al.; "Characterization and engineering of a DNA polymerase reveals a single amino-acid substitution in the fingers subdomain to increase strand-displacement activity of A-family prokaryotic DNA polymerases"; BMC Molecular and Cell Biology, vol. 20, Article No. 31; 2019; pp. 1-11.

Sievers, F. et al.; "Clustal Omega for making accurate alignments of many protein sequences"; Protein Science, vol. 27; 2018; pp. 135-145.

Singh, K. et al.; "Participation of the Fingers Subdomain of Escherichia coli DNA Polymerase I in the Strand Displacement Synthesis of DNA"; Journal of Biological Chemistry, vol. 282, Issue No. 14; 2007; pp. 10594-10604.

Summerer, D.; "DNA Polymerase Profiling"; Methods of Molecular Biology, vol. 429; 2008; pp. 225-235; DOI:10.1007/978-1-60327-040-3_16.

Walker, G.; "Empirical aspects of strand displacement amplification"; PCR Methods Appl., vol. 3; 1993; pp. 1-6.

* cited by examiner

```
   1 F  D  K  S  K  Y  E  C  V  Q  D  V  E  R  L  Q  H  W  V  D
   1 TTCGACAAAAGCAAATATGAGTGCGTTCAGGATGTTGAACGTCTGCAGCATTGGGTTGAT
  21 R  C  T  D  V  G  Y  C  A  V  D  L  E  T  D  S  L  D  S  A
  61 CGTTGTACCGATGTTGGTTATTGTGCAGTTGATCTGGAAACCGATAGCCTGGATAGCGCA
  41 A  A  N  L  V  G  V  C  L  A  V  A  D  N  E  A  C  Y  I  P
 121 GCAGCAAATCTGGTTGGTGTTTGTCTGGCAGTTGCAGATAATGAAGCATGTTATATTCCG
  61 L  G  H  T  G  G  G  D  L  L  G  D  G  A  P  E  Q  I  P  M
 181 CTGGGTCATACCGGTGGTGGTGATCTGCTTGGTGATGGTGCACCGGAACAAATTCCGATG
  81 Q  T  A  L  D  V  L  E  P  M  L  H  N  A  A  V  L  K  I  G
 241 CAGACCGCACTGGATGTTCTGGAACCGATGCTGCATAATGCCGCAGTTCTGAAAATTGGC
 101 Q  N  F  K  Y  D  L  G  V  F  Q  R  Y  G  L  Q  P  A  P  Y
 301 CAGAACTTCAAATATGATCTGGGTGTGTTTCAGCGTTATGGTCTGCAGCCTGCACCGTAT
 121 D  D  T  M  L  I  S  Y  A  L  S  C  G  L  H  S  H  G  M  D
 361 GATGATACCATGCTGATTAGCTATGCACTGAGCTGTGGTCTGCATAGCCATGGTATGGAT
 141 N  L  S  E  M  Y  F  D  H  K  P  I  P  F  K  E  L  V  G  S
 421 AATCTGAGCGAAATGTATTTCGACCATAAACCGATTCCGTTCAAAGAACTGGTTGGTAGC
 161 G  K  S  Q  K  T  F  N  Q  L  S  L  E  E  S  T  P  Y  A  A
 481 GGTAAAAGCCAGAAAACCTTTAATCAGCTGAGCCTGGAAGAAAGCACCCCGTATGCAGCC
 181 E  D  A  D  V  T  L  R  L  W  K  L  L  K  P  R  L  A  S  E
 541 GAAGATGCAGATGTTACCCTGCGTCTGTGGAAACTGCTGAAACCGCGTCTGGCAAGCGAA
 201 N  V  A  S  V  Y  E  T  L  E  R  G  M  P  S  V  L  A  M  M
 601 AATGTTGCAAGCGTTTATGAAACCCTGGAACGTGGTATGCCGAGCGTTCTGGCAATGATG
 221 E  N  N  G  I  K  V  D  K  A  V  L  A  R  L  S  G  D  F  E
 661 GAAAATAATGGTATCAAAGTGGATAAAGCGGTTCTGGCACGTCTGAGCGGTGATTTTGAA
 241 Q  K  K  A  G  L  E  A  E  A  H  E  L  A  G  R  S  F  N  L
 721 CAGAAAAAAGCAGGTCTGGAAGCCGAAGCACATGAACTGGCAGGTCGTTCATTTAATCTG
 261 G  S  P  K  Q  L  G  E  I  L  F  D  E  L  G  L  S  G  G  K
 781 GGTAGCCCGAAACAGCTGGGTGAAATTCTGTTTGATGAACTGGGTCTGAGTGGTGGCAAA
 281 K  T  K  T  G  A  W  Q  T  G  A  G  I  L  E  A  L  E  H  V
 841 AAAACCAAAACCGGTGCATGGCAGACCGGTGCAGGTATTCTGGAAGCACTGGAACATGTG
 301 H  P  L  P  K  A  I  L  E  W  R  H  Y  A  K  L  K  S  T  Y
 901 CATCCGCTGCCGAAAGCAATTCTGGAATGGCGTCATTATGCAAAACTGAAAAGCACCTAT
 321 T  D  T  L  P  Q  Q  I  N  A  R  T  G  R  V  H  T  S  Y  S
 961 ACCGATACACTGCCGCAGCAGATTAATGCACGTACCGGTCGTGTTCATACCAGCTATAGC
 341 L  A  S  T  S  T  G  R  L  S  S  S  D  P  N  L  Q  N  I  P
1021 CTGGCAAGCACCAGCACCGGTCGTCTGAGCAGCAGCGATCCGAATCTGCAGAATATTCCG
 361 I  R  T  E  D  G  R  K  I  R  T  A  F  I  A  E  P  G  N  I
1081 ATTCGTACCGAAGATGGTCGTAAAATTCGCACCGCATTTATTGCAGAACCGGGTAATATT
 381 L  V  A  A  D  Y  S  Q  V  E  L  R  I  L  A  H  V  A  D  L
1141 CTGGTTGCAGCCGATTATAGCCAGGTTGAACTGCGTATTCTGGCACATGTTGCAGATCTG
 401 T  N  M  K  Q  A  F  A  D  G  V  D  I  H  A  L  T  A  S  E
1201 ACCAATATGAAACAGGCATTTGCAGATGGTGTTGATATTCATGCACTGACCGCAAGTGAA
 421 M  F  G  V  P  I  D  G  M  D  S  S  V  R  R  R  A  K  A  I
1261 ATGTTTGGTGTTCCGATTGATGGCATGGATAGCAGCGTTCGTCGTCGTGCAAAAGCAATT
 441 N  F  G  I  I  Y  G  I  S  A  F  G  L  A  N  N  L  G  I  S
1321 AACTTTGGTATTATCTATGGCATCAGCGCATTTGGTCTGGCAAATAATCTGGGCATTAGC
 461 R  T  E  A  K  E  Y  I  D  S  Y  F  E  K  F  P  G  I  K  T
1381 CGCACCGAAGCAAAAGAATATATCGATAGCTACTTCGAGAAGTTCCCTGGCATTAAAACC
 481 Y  M  E  S  A  K  D  E  A  R  E  N  G  F  V  K  T  I  F  G
1441 TATATGGAAAGCGCAAAAGATGAAGCCCGTGAAAATGGTTTTGTGAAAACGATTTTTGGT
 501 R  K  C  H  I  K  G  I  N  D  K  N  G  A  M  R  G  F  G  E
1501 CGCAAGTGCCATATTAAAGGCATCAACGATAAAAATGGTGCCATGCGTGGTTTTGGTGAA
 521 R  Q  A  I  N  A  P  I  Q  G  A  A  A  D  I  M  R  R  A  M
1561 CGTCAGGCAATTAACGCACCGATTCAGGGTGCAGCAGCAGATATTATGCGTCGTGCCATG
 541 I  R  M  P  N  A  I  S  N  I  E  N  A  R  M  L  L  Q  V  H
1621 ATTCGTATGCCGAATGCCATTAGCAATATTGAAAATGCCCGTATGCTGCTTCAGGTTCAT
 561 D  E  L  V  F  E  V  P  E  A  S  A  E  A  L  I  K  T  V  K
1681 GATGAGCTGGTTTTTGAAGTGCCGGAAGCAAGCGCAGAAGCACTGATTAAAACCGTTAAA
 581 S  V  M  Q  N  A  C  A  P  A  V  H  L  S  V  P  L  V  V  D
1741 AGCGTTATGCAGAATGCATGTGCACCGGCAGTTCATCTGAGCGTTCCGCTGGTTGTTGAT

 601 A  K  A  A  H  N  W  N  D  A  H  *
1801 GCAAAAGCCGCACATAATTGGAATGATGCCCATTAA
```

FIG. 2

SEQUENCE LISTING

```
<160> NUMBER OF SEQ ID NOS: 13

<210> SEQ ID NO 1
<211> LENGTH: 611
<212> TYPE: PRT
<213> ORGANISM: Artificial Sequence
<220> FEATURE:
<223> OTHER INFORMATION: Marine large fragment DNA polymerase I with
      variable amino acid positions
<220> FEATURE:
```

<221> NAME/KEY: misc_feature
<222> LOCATION: (449)..(451)
<223> OTHER INFORMATION: Xaa can be any naturally occurring amino acid
<220> FEATURE:
<221> NAME/KEY: misc_feature
<222> LOCATION: (521)..(521)
<223> OTHER INFORMATION: Xaa can be any naturally occurring amino acid

<400> SEQUENCE: 1

```
Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365
```

```
Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Xaa Xaa Xaa Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Xaa Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610
```

<210> SEQ ID NO 2
<211> LENGTH: 611
<212> TYPE: PRT
<213> ORGANISM: Artificial Sequence
<220> FEATURE:
<223> OTHER INFORMATION: Wild type sequence of marine large fragment DNA polymerase I

<400> SEQUENCE: 2

```
Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110
```

```
Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ser Ala Phe Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
        515                 520                 525
```

```
Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610


<210> SEQ ID NO 3
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 3

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270
```

```
Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ser Asp Phe Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610
```

<210> SEQ ID NO 4
<211> LENGTH: 611
<212> TYPE: PRT
<213> ORGANISM: Artificial Sequence
<220> FEATURE:
<223> OTHER INFORMATION: Marine large fragment DNA polymerase I modified by mutagenesis

<400> SEQUENCE: 4

```
Phe Asp Lys Ser Lys Tyr Glu Cys Val Gln Asp Val Glu Arg Leu Gln
```

```
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430
```

```
Val Arg Arg Arg Ala Lys Ala Ile Asn Phe Gly Ile Ile Tyr Gly Ile
        435                 440                 445

Ala Ala Ala Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610


<210> SEQ ID NO 5
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 5

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
```

```
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ala Asp Phe Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590
```

```
Leu Ser Val Pro Leu Val Val Asp Ala Lys Ala Ala His Asn Trp Asn
        595                 600                 605

Asp Ala His
    610


<210> SEQ ID NO 6
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 6

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
```

```
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ser Asp Ala Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610


<210> SEQ ID NO 7
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 7

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60
```

```
Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220

Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ala Asp Ala Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
```

```
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Arg Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610


<210> SEQ ID NO 8
<211> LENGTH: 611
<212> TYPE: PRT
<213> ORGANISM: Artificial Sequence
<220> FEATURE:
<223> OTHER INFORMATION: Marine large fragment DNA polymerase I modified
      by mutagenesis

<400> SEQUENCE: 8

Phe Asp Lys Ser Lys Tyr Glu Cys Val Gln Asp Val Glu Arg Leu Gln
1               5                   10                  15

His Trp Val Asp Arg Cys Thr Asp Val Gly Tyr Cys Ala Val Asp Leu
            20                  25                  30

Glu Thr Asp Ser Leu Asp Ser Ala Ala Ala Asn Leu Val Gly Val Cys
        35                  40                  45

Leu Ala Val Ala Asp Asn Glu Ala Cys Tyr Ile Pro Leu Gly His Thr
    50                  55                  60

Gly Gly Gly Asp Leu Leu Gly Asp Gly Ala Pro Glu Gln Ile Pro Met
65                  70                  75                  80

Gln Thr Ala Leu Asp Val Leu Glu Pro Met Leu His Asn Ala Ala Val
                85                  90                  95

Leu Lys Ile Gly Gln Asn Phe Lys Tyr Asp Leu Gly Val Phe Gln Arg
            100                 105                 110

Tyr Gly Leu Gln Pro Ala Pro Tyr Asp Asp Thr Met Leu Ile Ser Tyr
        115                 120                 125

Ala Leu Ser Cys Gly Leu His Ser His Gly Met Asp Asn Leu Ser Glu
    130                 135                 140

Met Tyr Phe Asp His Lys Pro Ile Pro Phe Lys Glu Leu Val Gly Ser
145                 150                 155                 160

Gly Lys Ser Gln Lys Thr Phe Asn Gln Leu Ser Leu Glu Glu Ser Thr
                165                 170                 175

Pro Tyr Ala Ala Glu Asp Ala Asp Val Thr Leu Arg Leu Trp Lys Leu
            180                 185                 190

Leu Lys Pro Arg Leu Ala Ser Glu Asn Val Ala Ser Val Tyr Glu Thr
        195                 200                 205

Leu Glu Arg Gly Met Pro Ser Val Leu Ala Met Met Glu Asn Asn Gly
    210                 215                 220
```

```
Ile Lys Val Asp Lys Ala Val Leu Ala Arg Leu Ser Gly Asp Phe Glu
225                 230                 235                 240

Gln Lys Lys Ala Gly Leu Glu Ala Glu Ala His Glu Leu Ala Gly Arg
                245                 250                 255

Ser Phe Asn Leu Gly Ser Pro Lys Gln Leu Gly Glu Ile Leu Phe Asp
            260                 265                 270

Glu Leu Gly Leu Ser Gly Gly Lys Lys Thr Lys Thr Gly Ala Trp Gln
        275                 280                 285

Thr Gly Ala Gly Ile Leu Glu Ala Leu Glu His Val His Pro Leu Pro
    290                 295                 300

Lys Ala Ile Leu Glu Trp Arg His Tyr Ala Lys Leu Lys Ser Thr Tyr
305                 310                 315                 320

Thr Asp Thr Leu Pro Gln Gln Ile Asn Ala Arg Thr Gly Arg Val His
                325                 330                 335

Thr Ser Tyr Ser Leu Ala Ser Thr Ser Thr Gly Arg Leu Ser Ser Ser
            340                 345                 350

Asp Pro Asn Leu Gln Asn Ile Pro Ile Arg Thr Glu Asp Gly Arg Lys
        355                 360                 365

Ile Arg Thr Ala Phe Ile Ala Glu Pro Gly Asn Ile Leu Val Ala Ala
    370                 375                 380

Asp Tyr Ser Gln Val Glu Leu Arg Ile Leu Ala His Val Ala Asp Leu
385                 390                 395                 400

Thr Asn Met Lys Gln Ala Phe Ala Asp Gly Val Asp Ile His Ala Leu
                405                 410                 415

Thr Ala Ser Glu Met Phe Gly Val Pro Ile Asp Gly Met Asp Ser Ser
            420                 425                 430

Val Arg Arg Arg Ala Lys Ala Ile Asn Phe Gly Ile Ile Tyr Gly Ile
        435                 440                 445

Ser Ala Phe Gly Leu Ala Asn Asn Leu Gly Ile Ser Arg Thr Glu Ala
    450                 455                 460

Lys Glu Tyr Ile Asp Ser Tyr Phe Glu Lys Phe Pro Gly Ile Lys Thr
465                 470                 475                 480

Tyr Met Glu Ser Ala Lys Asp Glu Ala Arg Glu Asn Gly Phe Val Lys
                485                 490                 495

Thr Ile Phe Gly Arg Lys Cys His Ile Lys Gly Ile Asn Asp Lys Asn
            500                 505                 510

Gly Ala Met Arg Gly Phe Gly Glu Ala Gln Ala Ile Asn Ala Pro Ile
        515                 520                 525

Gln Gly Ala Ala Ala Asp Ile Met Arg Arg Ala Met Ile Arg Met Pro
    530                 535                 540

Asn Ala Ile Ser Asn Ile Glu Asn Ala Arg Met Leu Leu Gln Val His
545                 550                 555                 560

Asp Glu Leu Val Phe Glu Val Pro Glu Ala Ser Ala Glu Ala Leu Ile
                565                 570                 575

Lys Thr Val Lys Ser Val Met Gln Asn Ala Cys Ala Pro Ala Val His
            580                 585                 590

Leu Ser Val Pro Leu Val Val Asp Ala Lys Ala Ala His Asn Trp Asn
        595                 600                 605

Asp Ala His
    610
```

<210> SEQ ID NO 9
<211> LENGTH: 1836
<212> TYPE: DNA

<213> ORGANISM: Artificial Sequence
<220> FEATURE:
<223> OTHER INFORMATION: Marine large fragment DNA polymerase I, codon optimized

<400> SEQUENCE: 9

```
ttcgacaaaa gcaaatatga gtgcgttcag gatgttgaac gtctgcagca ttgggttgat     60
cgttgtaccg atgttggtta ttgtgcagtt gatctggaaa ccgatagcct ggatagcgca    120
gcagcaaatc tggttggtgt ttgtctggca gttgcagata atgaagcatg ttatattccg    180
ctgggtcata ccggtggtgg tgatctgctt ggtgatggtg caccggaaca aattccgatg    240
cagaccgcac tggatgttct ggaaccgatg ctgcataatg ccgcagttct gaaaattggc    300
cagaacttca aatatgatct gggtgtgttt cagcgttatg gtctgcagcc tgcaccgtat    360
gatgatacca tgctgattag ctatgcactg agctgtggtc tgcatagcca tggtatggat    420
aatctgagcg aaatgtattt cgaccataaa ccgattccgt tcaaagaact ggttggtagc    480
ggtaaaagcc agaaaacctt taatcagctg agcctggaag aaagcacccc gtatgcagcc    540
gaagatgcag atgttaccct gcgtctgtgg aaactgctga aaccgcgtct ggcaagcgaa    600
aatgttgcaa gcgtttatga aaccctggaa cgtggtatgc cgagcgttct ggcaatgatg    660
gaaaataatg gtatcaaagt ggataaagcg gttctggcac gtctgagcgg tgattttgaa    720
cagaaaaaag caggtctgga agccgaagca catgaactgg caggtcgttc atttaatctg    780
ggtagcccga aacagctggg tgaaattctg tttgatgaac tgggtctgag tggtggcaaa    840
aaaaccaaaa ccggtgcatg gcagaccggt gcaggtattc tggaagcact ggaacatgtg    900
catccgctgc cgaaagcaat tctggaatgg cgtcattatg caaaactgaa aagcacctat    960
accgatacac tgccgcagca gattaatgca cgtaccggtc gtgttcatac cagctatagc   1020
ctggcaagca ccagcaccgg tcgtctgagc agcagcgatc cgaatctgca gaatattccg   1080
attcgtaccg aagatggtcg taaaattcgc accgcattta ttgcagaacc gggtaatatt   1140
ctggttgcag ccgattatag ccaggttgaa ctgcgtattc tggcacatgt tgcagatctg   1200
accaatatga aacaggcatt tgcagatggt gttgatattc atgcactgac cgcaagtgaa   1260
atgtttggtg ttccgattga tggcatggat agcagcgttc gtcgtcgtgc aaaagcaatt   1320
aactttggta ttatctatgg catcagcgca tttggtctgg caaataatct gggcattagc   1380
cgcaccgaag caaaagaata tatcgatagc tacttcgaga agttccctgg cattaaaacc   1440
tatatggaaa gcgcaaaaga tgaagcccgt gaaaatggtt ttgtgaaaac gatttttggt   1500
cgcaagtgcc atattaaagg catcaacgat aaaaatggtg ccatgcgtgg ttttggtgaa   1560
cgtcaggcaa ttaacgcacc gattcagggt gcagcagcag atattatgcg tcgtgccatg   1620
attcgtatgc cgaatgccat tagcaatatt gaaaatgccc gtatgctgct tcaggttcat   1680
gatgagctgg tttttgaagt gccggaagca agcgcagaag cactgattaa aaccgttaaa   1740
agcgttatgc agaatgcatg tgcaccggca gttcatctga gcgttccgct ggttgttgat   1800
gcaaaagccg cacataattg gaatgatgcc cattaa                              1836
```

<210> SEQ ID NO 10
<211> LENGTH: 82
<212> TYPE: DNA
<213> ORGANISM: Artificial Sequence
<220> FEATURE:
<223> OTHER INFORMATION: Synthetic molecular beacon template

<400> SEQUENCE: 10

-continued

```
ggcccgtagg aggaaaggac atcttctagc atacgggccg tcaagttcat ggccagtcaa      60

gtcgtcagaa atttcgcacc ac                                               82


<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11

gtggtgcgaa atttctgac                                                   19


<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12

tatccaccaa tactaccctc gatactttgt ccactcaat                             39


<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13

ataggtggtt atgatgggat gctatgaaac aggtgagtta                            40
```

MARINE DNA POLYMERASE I

CROSS REFERENCE TO RELATED APPLICATIONS

This application is a National Stage application of PCT/EP2020/077534, filed Oct. 1, 2020, which claims priority to European Patent Application No. 19200782.1, filed Oct. 1, 2019, both of which are incorporated by reference in their entirety herein.

SEQUENCE LISTING

The Instant Application contains a Sequence Listing which has been submitted electronically in ASCII format and is hereby incorporated by reference in its entirety. Said ASCII copy, created on Sep. 13, 2022 is named "OSA0069US Replacement Sequence List_ST25" and is 46,862 bytes in size.

FILED OF INVENTION

The present invention relates to DNA polymerases. In particular, the present invention relates to heat labile DNA polymerases of marine origin. Furthermore, the present invention provides heat labile DNA polymerases substantially without strand-displacement activity. The present invention furthermore relates to the use of said DNA polymerase in various molecular biology processes.

BACKGROUND OF THE INVENTION

Synthetic biology is a rapidly evolving field and is heralded as a possible solution for the challenges in future bio-economy and bioenergy. The ultimate vision of synthetic biology is to create new biological operating systems of cells that predictably can carry out useful tasks. One of the key steps in a synthetic biology pipeline is the assembly of DNA fragments into larger functional constructs often involving multiple assemblies.

A current bottleneck is however the lack of a robust room-temperature method to do multiple DNA assemblies without time-consuming manual treatment steps. A new DNA assembly method able to bypass the current hurdles is therefore highly desired.

Replication of genomic DNA is the primary function of DNA polymerases, catalysing the synthesis for polydeoxyribonucleotides from mono-deoxyribonucleoside triphosphate (dNTPs).

In vitro, the characteristics of DNA polymerases are used in DNA synthesis, such as in various DNA amplification processes, DNA assembly processes and in synthesis of DNA molecules reading a DNA strand template of interest creating two new DNA strands that match the template.

Different types of polymerases are found. For example, in *E. coli* and other prokaryotic cells, the known DNA polymerases are commonly referred to as DNA polymerase I-V. The various groups vary in fidelity of replication, thermostability, elongation rate, and proof-reading activity and efficiency. Some DNA polymerases are rather simple and others more complex, such as *E. coli* polymerase III that consist of 20 different peptide subunits. When used in DNA replication processes in vitro, in addition to dNTPs, a primer (an initial oligonucleotide) is needed, carrying a 3'end hydroxyl group that can be used as the starting point of chain growth, since DNA polymerases cannot initiate synthesis de novo from mononucleotides. The primer can be a short or long piece of DNA or RNA which carries a free 3'-OH group, providing a double-stranded structure to the DNA polymerase by annealing to a complementary region of a template. The selected DNA polymerase works along the template, extending the primer in the 5'→3' direction.

Because of DNA strand polarity, replication of the two strands of a DNA molecule are bidirectional resulting in in two distinct products, a "leading" and a "lagging" strands, according to the direction of the replication of the template. The leading strand is synthesized as a single continuous chain, whereas the lagging strand is initially synthesized as small oligonucleotides, called Okazaki fragments, which are then ligated to form a continuous chain. In vivo, small RNA molecules work as natural primers in the synthesis of both the leading strand and, in particular, the lagging strand.

It is well known that DNA polymerase III synthesize continuously the leading strand and also the Okazaki fragments on the lagging strand, leaving gaps between the synthesized fragments that are thereafter filled by DNA polymerase I.

In addition to the DNA synthesis activity, DNA polymerases may also exert other enzyme activities, such as 3'-5' exonuclease activities or strand displacement activities. The role of the strand replacement activity of DNA polymerases is to remove initiator RNA or primer before ligation. In vivo, the 3'-5' exonuclease activity of some of the DNA polymerases is important for genetic stability, correcting DNA polymerase errors, that e.g. results in mismatched base pair in the resulting DNA molecule that is then corrected by the exonuclease function of DNA polymerases.

Piotrowski, Y. et al., Molecular and Cell biology, 2019, page 1-11 and Singh, K. et al., J. of Biological Chemistry, 2007, vol. 282, no. 14, page 10594-10604 disclose mutant DNA polymerases with altered strand displacement activity.

In order to substitute and correct a mismatched base pair, the proof reading activity of DNA polymerases must be able to remove the incorrectly introduced dNTP and the nuclease activity are therefore involved in breaking of the phosphodiester bond in the phosphate backbone of DNA molecules. The ability to remove a mismatched dNTP and thus degrade DNA is utilized in various ways in in vitro molecular biology. Sequence specific DNA amplification has many applications in molecular biology, such as in determination of paternity, forensic investigations and in diagnostics. Many of the widely used DNA polymerases are stable at high temperatures, such as up to at least 70° C., thus enabling their use in DNA detection and analysis methods, such as polymerase chain reaction (PCR) or thermocycled DNA sequencing. DNA polymerases applicable in such processes are commonly named thermostable DNA polymerases.

PCR is based on thermal cycling to denature template DNA, annealing of primers and extend the primers using thermostable DNA polymerases that withstands the varying temperature conditions and by amplification exponentially increase the amount of the DNA of interest. Other amplification methods are isothermal, i.e. are carried out at a constant temperature. Today, a variety of isothermal DNA amplification methods exist, e.g. strand displacement amplification (cf. e.g. Walker G T. Empirical aspects of strand displacement amplification. PCR Methods Appl. 1993; 3: 1-6) and loop-mediated amplification (LAMP) (cf. e.g. Notomi T, Okayama H, Masubuchi H, Yonekawa T, Watanabe K, Amino N, et al. Loop-mediated isothermal amplification of DNA. Nucleic Acids Res. 2000; 28: E63). DNA polymerases useful in strand displacement amplification are commercially available, such as the EquiPhi29™ DNA Polymerase provided by ThermoFisher Scientific.

DNA polymerases are also used in DNA assembly processes, such as the Gibson Assembly® method, described by Gibson et al. in Nature Methods, 2009, vol. 6, pp. 343-345, allowing for a single step isotherm assembly of nucleic acid molecules. The method, however requires that the process is performed at 50° C.

A current bottleneck is however the lack of a robust room-temperature method to do multiple DNA assemblies without time-consuming manual treatment steps. For example, when using PCR products in DNA assembly methods, the products must be purified (subjected to clean up procedures) before they can be used in multiple DNA assembly processes. Purification step are also required if several rounds of assembling are needed. A new DNA assembly method able to bypass the current hurdles is therefore highly desired.

Various enzymes of marine origin are known. For example, WO2017/162765 discloses a thermostable DNA polymerase of marine origin isolated from *Psychrobacillus* sp. being active at a wide range of temperatures, including temperatures above room temperature.

WO2016026574 discloses a thermolabile exonuclease originating from a cold-water environment being capable of degrading single stranded DNA, and which may be inactivated within 15-20 minutes if exposed to temperatures below 65° C.

The present inventors have identified a DNA polymerase I by metagenomic analysis of marine environmental samples collected in the marine artic area around Svalbard. Unlike other known DNA polymerases, the present isolated DNA polymerases are intrinsically heat labile which renders the enzymes specifically useful in molecular biology processes, such as in a variety of DNA amplification processes and DNA assembly processes. For example, the present DNA polymerase is rapidly and irreversible inactivated at temperatures above 25° C., such as at temperatures above about 30° C., resulting in no need for any inactivation step before further handling of a product being subjected to the DNA polymerase of the present invention.

In addition, the present inventors have shown that the present DNA polymerase exert a very robust polymerase activity compared with commercially available DNA polymerases, such as the mesophilic Klenow enzyme from *E. coli* and the thermophilic Bst polymerase originating from *Bacillus stearothermophilus*.

The robust polymerase activity as well as the temperature lability characteristics of the present DNA polymerase makes it a very useful DNA polymerase for a wide range of DNA amplification processes, which can be performed at room-temperature and which avoids the need of an inactivation step.

The present DNA polymerase furthermore exerts 3'-5' exonuclease activity, resulting in proof reading of the replicated DNA molecule.

The present DNA polymerase furthermore possesses a strand displacement activity, making it an attractive polymerase for strand displacement amplification processes The present inventors have also synthesized modified variants of the DNA polymerase of the present invention, wherein the strand displacement activity of the DNA polymerase is sufficiently impaired or absent.

The modified DNA polymerases of the present invention with impaired or lacking strand displacement activity is in particularly useful in recombinant cloning processes, e.g. wherein two or more double stranded nucleic acid molecules with single stranded 5' overhang is assembled. In particular, a modified DNA polymerase with impaired or lacking strand displacement activity is useful in multiple DNA assembly methods, and because of its heat liability renders it possible to work at room temperature. A further advantage of the present DNA polymerase is that when used in DNA amplification or DNA assembly processes, as shown further below, no inactivation step deemed is necessary.

SUMMARY OF THE INVENTION

According to a first aspect, an isolated DNA polymerase or an enzymatically active fragment thereof is provided, wherein said DNA polymerase exert strand-displacement activity, 3'-5' exonuclease activity, and wherein said DNA polymerase is irreversibly inactivated at temperatures above 25° C., more preferably at temperatures above about 30° C.

According to one embodiment of this aspect, a DNA polymerase is provided wherein the strand displacement activity is reduced, impaired or inactivated.

According to second aspect of the present invention, an isolated DNA polymerase or an enzymatically active fragment thereof is provided, said DNA polymerase comprising the amino acid sequence of SEQ ID No. 1, or comprising an amino acid sequence which is at least 60% sequence identical over the entire length of the sequence with SEQ ID No. 1.

According to a third aspect of the present invention, an isolated DNA polymerase or an enzymatically active fragment thereof is provided, said DNA polymerase comprising the amino acid sequence of SEQ ID No. 2, or comprising an amino acid sequence which is at least 60% sequence identical over the entire length of the sequence with SEQ ID No. 2.

The isolated DNA polymerase or an enzymatically active fragment thereof according to the above aspects may comprise an amino acid sequence which is at least 70% identical over the entire length of the sequence with SEQ ID No. 1 or SEQ ID No. 2, such as at least 80% sequence identical over the entire length of the sequence with SEQ ID No. 1 or SEQ ID No. 2, such as at least 90% sequence identical over the entire length of the sequence with SEQ ID No. 1 or SEQ ID No. 2.

According to a fourth aspect, an isolated DNA polymerase or an enzymatically active fragment thereof is provided, wherein said amino acid sequence comprises at least one mutation in at least one of the amino acid regions corresponding to amino acid positions 431-447 and positions 519-523, the numbering being accordance with the amino acid numbering in SEQ ID NO. 2, and wherein said DNA polymerase have no strand-displacement activity. For example, said DNA polymerase or an enzymatically active fragment thereof comprises at least one mutation in amino acid positions corresponding to S449, A450, F451, and/or R521 of an amino acid sequence as set forth in SEQ ID No. 1 and SEQ ID No. 2.

According to a fifth aspect, an isolated DNA polymerase or an enzymatically active fragment thereof is provided, wherein said DNA polymerase comprises at least one mutation in amino acid positions corresponding to S449, A450, F451, and/or R521 of an amino acid sequence as set forth in SEQ ID No. 1 and SEQ ID No. 2, and wherein the at least one mutation is a substitution to:

- an amino acid with a hydrophobic side chain at a position corresponding to S449,
- an amino acid with a negative charged side chain at a position corresponding to A450, an amino acid with a hydrophobic side chain at a position corresponding to F451, and/or an amino acid with a hydrophobic side chain at a position corresponding to R521.

For example, said isolated DNA polymerase or an enzymatically active fragment thereof may according to one embodiment of the above aspect comprise an amino acid sequence wherein the amino acid in position 449 according to the numbering of SEQ ID No. 1 or SEQ ID No. 2 is selected from the group consisting of Ser, Ala, Gly, Val, Leu, Ile.

Furthermore, said isolated DNA polymerase or an enzymatically active fragment thereof may according to one embodiment of the above aspect, comprises an amino acid sequence, wherein the amino acid in position 450 according to the numbering of SEQ ID No. 1 or SEQ ID No. 2 is selected from the group consisting of Ala, Gly, Val, Leu, Ile, Asp, Glu, Asn, Gln.

Furthermore, said isolated DNA polymerase or an enzymatically active fragment thereof may according to one embodiment of the above aspect, comprises an amino acid sequence, wherein the amino acid in position 451 according to the numbering of SEQ ID No. 1 or SEQ ID No. 2 is selected from the group consisting of Phe, Ala, Gly, Val, Leu, Ile.

Furthermore, said isolated DNA polymerase or an enzymatically active fragment thereof may according to one embodiment of the above aspect, comprises an amino acid sequence, wherein the amino acid in position 521 according to the numbering of SEQ ID No. 1 or SEQ ID No. 2 is selected from the group consisting of Arg, Ala, Gly, Val, Leu, Ile.

Furthermore, said isolated DNA polymerase or an enzymatically active fragment thereof may according to one embodiment of the above aspect, comprises an amino acid sequence, wherein the amino acid in position 449, 450, 451 and 521 is selected from the groups consisting of

| Amino acid position of SEQ ID No. 1 | Amino acid |
|---|---|
| 449 | Ser, Ala, Gly, Val, Leu, Ile |
| 450 | Ala, Gly, Val, Leu, Ile, Asp, Glu, Asn, Gln |
| 451 | Phe, Ala, Gly, Val, Leu, Ile |
| 521 | Arg, Ala, Gly, Val, Leu, Ile |

provided that the amino acids in position 449 (S449), 450 (A450), 451 (F451) and 521 (R521) are not at the same time Ser, Ala, Phe and Arg, respectively.

Furthermore, said isolated DNA polymerase or an enzymatically active fragment thereof may according to one embodiment of the above aspect, comprises an amino acid sequence, wherein the amino acid in position 449, 450, 451 and 521 is selected from the groups consisting of

| Amino acid position of SEQ ID No. 1 | Amino acid |
|---|---|
| 449 | Ser, Ala |
| 450 | Ala, Asp |
| 451 | Phe, Ala |
| 521 | Arg, Ala |

and provided that the amino acids in position 449 (S449), 450 (A450), 451 (F451) and 521 (R521) is not at the same time Ser, Ala, Phe and Arg, respectively. In one embodiment according to any of the preceding aspects the isolated DNA polymerase or an enzymatically active fragment thereof is selected from a group of DNA polymerases comprising an amino acid sequence wherein the amino acid in position 450 is Asp, the amino acids in position 449 and 451 are Ala, the amino acids in position 449 and 450 are Ala and Asp, respectively, the amino acids in position 450 and 451 are Asp and Ala, respectively, the amino acids in position 449, 450 and 451 are Ala, Asp and Ala, respectively, the amino acid in position 521 in SEQ ID No. 8 is Ala and wherein the numbering is according to numbering of the amino acids of SEQ ID No. 1 and wherein any of said DNA polymerases has no strand strand-displacement activity.

According to a sixth aspect, an isolated DNA polymerase or an enzymatically active fragment thereof is provided, said DNA polymerase comprising the amino acid sequence selected from the group consisting of SEQ ID No. 3, 4, 5, 6, 7 and 8, or comprising an amino acid sequence which is at least 60% such as at least 70%, such as at least 75%, such as at least 80%, such as at least 85% such as at least 90%, such as at least 95%, such as at least 97%, such as at least 98% or 99% sequence identity over the entire length of the sequence with SEQ ID No. 3, 4, 5, 6, 7, and 8, respectively, provided that the amino acid in position 450 in SEQ ID No. 3 is Asp, the amino acids in position 449 and 451 in SEQ ID No. 4 are Ala, the amino acids in position 449 and 450 in SEQ ID No. 5 are Ala and Asp, respectively, the amino acids in position 450 and 451 in SEQ ID No. 6 are Asp and Ala, respectively, the amino acids in position 449, 450 and 451 in SEQ ID No. 7 are Ala, Asp and Ala, respectively, the amino acid in position 521 in SEQ ID No. 8 is Ala.

The present invention also provides according to any of the above aspects a DNA polymerase or an enzymatically active fragment thereof, wherein the enzyme is irreversibly inactivated at temperatures above 25° C., such as at temperatures above 30° C.

According to a seventh aspect, a composition is provided comprising an isolated DNA polymerase or an enzymatically active fragment thereof according to any of the preceding aspects and a buffer.

According to an embodiment of any of the above aspects the DNA polymerase is a large fragment DNA polymerase I lacking the N-terminal 5'-3'-exonuclease domain.

SEQ ID No. 1 and Seq ID No. 2 are examples of large fragment DNA polymerase sequences lacking the N-terminal 5'-3'-exonuclease domain.

According to a ninth aspect, a nucleic acid molecule is provided encoding an isolated DNA polymerase or an enzymatically active fragment thereof according to any of the above aspects. In one embodiment according to the above aspect the nucleic acid molecule comprises the nucleic acid sequence of SEQ ID No. 9 or comprising a nucleic acid molecule which has at least 60% sequence identity over the entire length of the sequence of SEQ ID No. 9.

In one embodiment according to the above aspect the nucleic acid molecule comprises a nucleic acid molecule encoding an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, and SEQ ID No. 8 or comprising a nucleic acid molecule encoding an amino acid sequence which has at least 60% sequence identity over the entire length of the sequence with SEQ ID No. 3, SEQ ID No. 4, SEQ ID No. 5, SEQ ID No. 6, SEQ ID No. 7, SEQ ID No. 8, respectively.

According to a tenth aspect, an expression vector is provided comprising a nucleic acid molecule encoding an isolated DNA polymerase or an enzymatically active fragment thereof according to the above aspects and the necessary regulatory sequences for the transcription and translation of the protein sequence encoded by said nucleic acid molecule.

Said expression vector may for example comprise a nucleic acid sequence encoding an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8 or comprising a nucleic acid molecule encoding an amino acid sequence which has at least 60% sequence identity over the entire length of the sequence with SEQ ID No. 3, SEQ ID No. 4, SEQ ID No. 5, SEQ ID No. 6, SEQ ID No. 7, SEQ ID No. 8, respectively.

According to an eleventh aspect, a host cell is provided comprising one or more expression vectors as mentioned above, or one or more nucleic acid molecules mentioned above encoding the DNA polymerase of the present invention.

According to a twelfth aspect, a method for preparation of a DNA polymerase or an enzymatically active fragment thereof according to the invention, comprising the steps of:

a) culturing a host cell comprising one or more of the recombinant expressions vectors according to according to the tenth aspect, or one or more nucleic acid molecules according to the ninth aspect under conditions suitable for the expression of the encoded DNA polymerase;

b) isolating or obtaining the DNA polymerase such as a large fragment DNA polymerase from the host cell or from the culture medium or supernatant.

According to a thirteenth aspect, the present invention furthermore relates to the use of a DNA polymerase such as a large fragment DNA polymerase or an enzymatically active fragment of the invention in a nucleic acid amplification process, sequencing reaction, recombinant cloning process or multiple DNA assembly processes.

According to one embodiment of this aspect, the DNA polymerase of the present invention is used in strand displacement amplification.

Furthermore, according to a fourteenth aspect, a method for assembly of two or more double stranded (ds) DNA molecules is provided, said process comprising the steps of:

(a) providing two or more dsDNA molecules to be assembled, wherein the dsDNA molecules comprise a single stranded (ss) DNA overhang, wherein the terminal ends including the overhangs of the two or more dsDNA molecules share regions of sequence identity;
(b) incubating the DNA molecules of (a) under conditions whereby said DNA molecules anneal through the overhang portions;
(c) contacting the annealed molecules with a heat labile DNA polymerase such as a large fragment DNA polymerase or an enzymatically active fragment thereof according to any of aspect one to sixth, whereby the DNA polymerase fill in the gaps remaining after the annealing of DNA molecules formed in step (b), wherein said DNA polymerase have reduced, impaired or inactivated strand displacement activity.

The steps (a)-(c) of the above method may be carried out at constant temperature. According to one embodiment, said process is carried out at a temperature within the range of 20° C. to 25° C.

According to another embodiment, the assembled DNA molecule of step (c) is further transferred into a suitable host cell for propagation.

According to a fifteenth aspect, a method is provided, wherein the overhang of the two or more DNA molecules of step (a) of the above method is provided using a 3'-5'exonuclease, preferably a heat labile exonuclease.

According to a sixteenth aspect, a method of nucleotide polymerization is provided using a DNA polymerase such as a large fragment DNA polymerase or enzymatically active fragment thereof of the invention, said method comprising the steps of:

(a) providing a reaction mixture comprising a DNA polymerase of the invention or enzymatically active fragment thereof, a template nucleic acid molecule, an oligonucleotide primer which is capable of annealing to a portion of the template nucleic acid molecule and one or more species of nucleotide; and
(b) incubating said reaction mixture under conditions whereby the oligonucleotide primer anneals to the template nucleic acid molecule and said DNA polymerase extends said oligonucleotide primer by polymerizing one or more nucleotides.

According to a seventeenth aspect, a method of amplifying a nucleic acid using a DNA polymerase such as a large fragment DNA polymerase or enzymatically active fragment thereof is provided, said method comprising the steps of:

(a) providing a reaction mixture comprising a DNA polymerase or enzymatically active fragment thereof according to any one aspects one to six, a template nucleic acid molecule, an oligonucleotide primer(s) which is capable of annealing to a portion of the template nucleic acid molecule acid molecule, and nucleotides;
(b) incubating said reaction mixture under conditions whereby the oligonucleotide primer(s) anneals to the template nucleic acid molecule and said DNA polymerase extends said oligonucleotide primer(s) by polymerizing one or more nucleotides to generate a polynucleotide.

FIGURES

FIG. 2 shows the DNA (SEQ ID NO: 9) and amino acid sequence (SEQ ID NO. 2) of the DNA polymerase of the present invention.

DETAILED DESCRIPTION OF THE INVENTION

Figure 1:
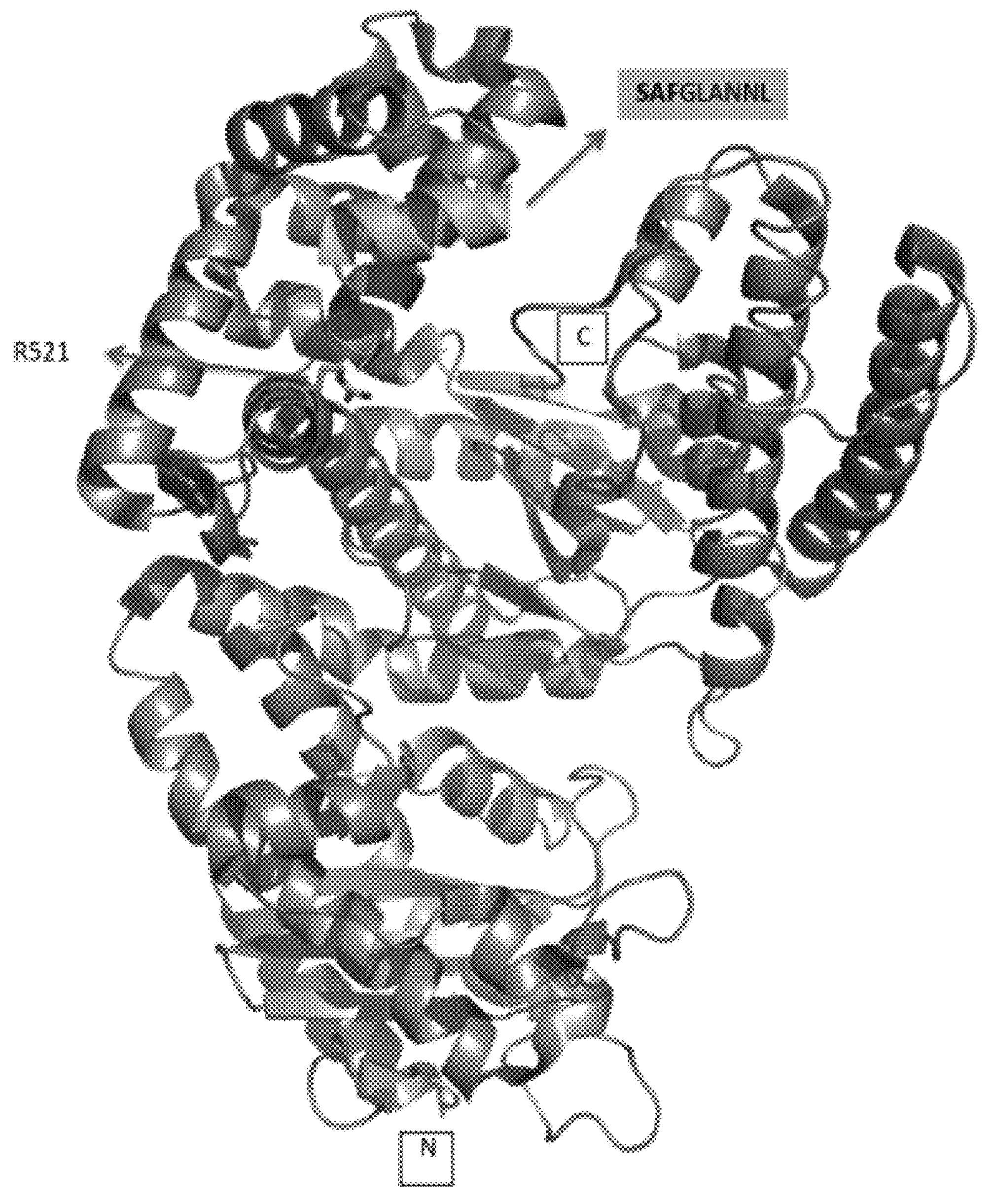
FIG. 1 represents the Klenow fragment (PDB code: 1D8Y), a homologous polymerase to the DNA polymerases of the present invention, illustrating the alpha helix identified by the arrow harboring the three consecutive amino acid residues S449, A450 and F451, and also showing the position of residue R521, the C- and N-terminal end.

The present inventors have as mentioned identified a novel DNA polymerase of marine origin with advantageous characteristics which makes said DNA polymerase and variants thereof useful in a number of molecular biology processes. In particular, it is advantageous that the enzyme may be used in processes carried out at room temperature, and that is it easily inactivated, such as at a temperature above 25° C., such as above 30° C.

Unless specifically defined herein, all technical and scientific terms used have the same meaning as commonly understood by a skilled artisan in the fields of genetics, biochemistry, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail.

Where a numeric limit or range is stated, the endpoints are included. Also, all values and sub ranges within a numerical limit or range are specifically included as if explicitly written out.

As will be shown below, the DNA polymerase of the invention may be used in order to provide assembly target nucleic acid molecules with 5'-3' overhang, e.g. in order to provide a full sequence nucleic acid molecule and combine said molecule with a vector. The DNA polymerase may thus be used to assembly one or more target nucleic acid molecule in a carrier or expression vector, wherein the desired nucleic acid molecule(s) and the vector has complementary 5'-3' overhang.

That is, upon contacting the one or more target double stranded nucleic acid molecule and a vector of choice, both having 5'-3' overhangs, e.g. of a length of about 10-40 base pair, the DNA polymerase of the present invention will fill in the number of nucleotides needed in order to assembly the sequences in questions. Due to the DNA polymerases heat liability, the DNA polymerase will be inactivated within a short time but is active for a sufficient time in order to e.g. assembly the nucleic acid molecules in question.

For example, the DNA polymerase of the present invention may become inactive over time at 25° C., however it has been shown to maintain its activity for at least 60 minutes, it does not influence further process steps e.g. when used in multiple DNA assembly methods. According to one embodiment, when used in multiple DNA assembly methods, annealed DNA molecules are brought in contact with a DNA polymerase with reduced, impaired or inactivated strand displacement activity, for a period of time in the range of 5-45 minutes, such as in the range of 10-30 minutes, such as in the range of 15-20 minutes.

The enzyme of the present invention may be used in various processes carried out at room temperature. The term "room temperature" is a recognized term in the art and includes temperatures in within the range of 18° C. to 25° C.

According to another aspect, a DNA polymerase or an enzymatically active fragment thereof is provided, comprising the amino acid sequence of SEQ ID No. 1 or SEQ ID NO. 2, or comprising an amino acid sequence which is at least 60% sequence identical over the entire length of the sequence with SEQ ID No. 1.

The expression "an enzymatically active fragment" of the DNA polymerase is to be understood to mean a DNA polymerase where the activity of the polymerase is maintained, that is having the same or at least similar activity compared with a DNA polymerases having an amino acid sequence as depicted in SEQ ID No. 1-8, although one or more amino acids are removed compared with the sequences depicted in SEQ ID No. 1-8. The skilled person will acknowledge that one or more amino acid may be removed, e.g. in the C- or N-terminal end of an amino acid sequence, without affecting the activity of the protein.

Figure 3:
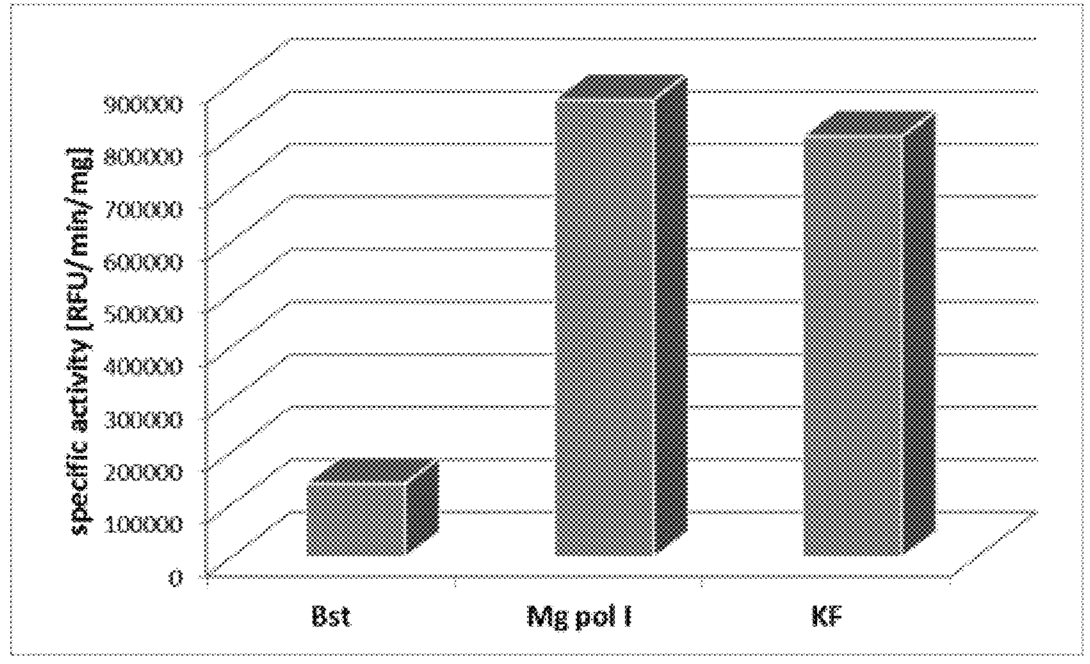
FIG. 3 shows the polymerase activity of the present large fragment DNA polymerase compared with the polymerase activity of the Klenow enzyme from *E. coli* and the thermophilic *Bacillus stearothermophilus* (Bst) polymerase.
Figure 4:
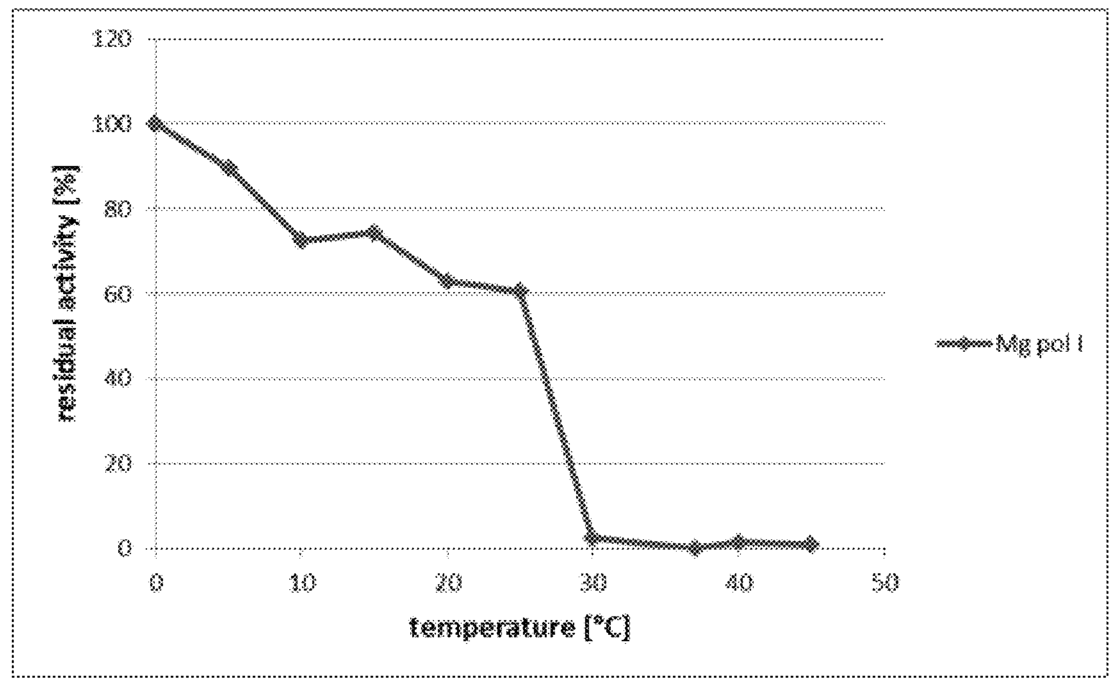
FIG. 4 shows the results of experiment measuring the residual activity of the present wild type large fragment DNA polymerase at 25° C. after incubation of the enzyme at various temperatures.

The DNA polymerase of the present invention exerts a superior polymerase efficiency compared with known DNA polymerases. As shown in FIG. 3, the present DNA polymerase show improved polymerase activity compared with the polymerase activity of the Klenow enzyme from *E. coli* and the thermophilic *Bacillus stearothermophilus* (Bst) polymerase. The skilled person will furthermore acknowledge that polymerase activity can be measured using a real time molecular beacon assay, such as disclosed in Summerer, *Methods Mol. Biol.,* 2008, 429, 225-235 or in modified form as shown in the below experimental part.

Figure 6:
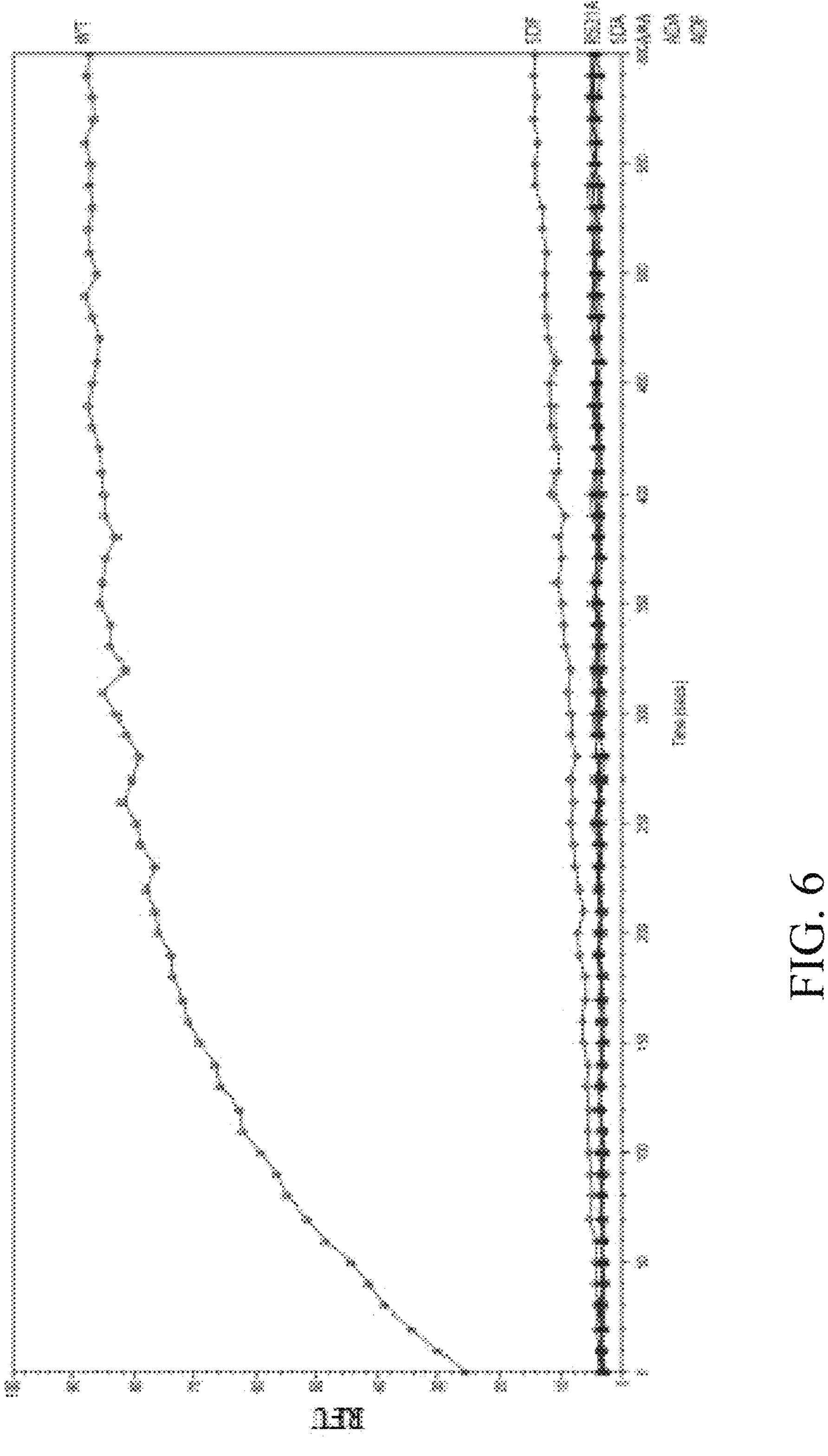
FIG. 6 shows a comparison of the strand displacement activity of the large fragment DNA polymerases of the present invention at 25° C., represented by the wild type (wt) DNA polymerase, the A450D-mutant (SDF), S449A+F451A-mutant (AAA), S449A+A450D-mutant (ADF), the A450D+F451A-mutant (SDA), the S449A+A450D+F451A-mutant (ADA) and the R521A-mutant.

According to a second aspect, a DNA polymerase is provided substantially without strand-displacement activity and wherein said DNA polymerase is substantially without strand-displacement activity and furthermore is irreversibly inactivated at temperatures above 25° C., such as temperatures above about 30° C. Reference is in this respect made to FIG. 6, showing that the modified DNA polymerases of the present invention possesses reduced strand displacement activity compared with the wild type DNA polymerase. The skilled person will acknowledge that strand displacement activity can be measured using well known methods, such as the strand displacement activity assay described in Piotrowski et al., 2019, BMC Mol Cell Biol, 20 (31).

The expression "substantially without strand displacement activity" is to be understood to mean that the displacement activity of the DNA polymerase is impaired or absent compared with the wild type DNA polymerase the wild type DNA polymerase having an amino acid sequence according to SEQ ID No. 2. For example, the skilled person will acknowledge that a DNA polymerase having a displacement activity that is reduced to the degree of the DNA polymerases having an amino acid sequence of SEQ ID NO. 3-8 has an impaired strand displacement activity, i.e. that are substantially without strand displacement activity.

According to yet another aspect, the present invention provides a DNA-polymerase such as an isolated large fragment DNA polymerase or an enzymatically active fragment thereof comprising an amino acid sequence of SEQ ID No. 1 or amino acid sequences that are at least 60% sequence identical over the entire length of the sequence with SEQ ID No. 1.

According to yet another aspect, the present invention provides a DNA-polymerase such as an isolated large fragment DNA polymerase or an enzymatically active fragment thereof comprising an amino acid sequence of SEQ ID No.

2 or amino acid sequences that are at least 60% sequence identical over the entire length of the sequence with SEQ ID No. 2.

As mentioned above, a DNA polymerase is provided comprising an amino acid according to SEQ ID No. 1 or SEQ ID No. 2 and comprising at least one mutation in the regions corresponding to amino acid positions 431-447 and positions 519-523, the numbering being accordance with the amino acid numbering in SEQ ID NO. 2, and wherein said DNA polymerase have no strand-displacement activity. The amino acids in position 431 to 447 make up three helixes believed to be involved in the strand displacement activity of the identified marine DNA polymerase of the present invention. According to one embodiment, a DNA polymerase is provided comprising an amino acid according to SEQ ID No. 1 or SEQ ID No. 2 and comprising at least one mutation in the regions corresponding to amino acid positions G447-L453 and positions G519-A523, the numbering being accordance with the amino acid numbering in SEQ ID NO. 2.

In particular, a DNA polymerase is provided wherein a mutation is introduced in position 449, 450, 451 and/or 521.

The present invention provides as examples wherein inter alia serine in position 449 is replaced by alanine, or wherein alanine in position 450 is replaced by asparagine, or wherein phenylalanine in position 451 is replaced by alanine, or wherein arginine in position 521 is replaced by alanine.

The skilled person will acknowledge that amino acids are grouped dependent upon the chemical characteristics of the side chain. Amino acids are commonly classified as hydrophobic or hydrophilic and/or as having polar or non-polar side chain.

Substitutions of one amino acid for another having the same biochemical characteristics are commonly known as conservative substitution. The skilled person will acknowledge that conservative substitutions can be introduced into an amino acid sequence of a protein, e.g. to the enzyme according to the present invention without altering the activity of said enzyme. Such modifications will thus be expected to constitute a biologically equivalent product.

Conservative substitution of amino acids include substitution made among amino acids within the following groups:

- Val, Ile, Leu, Met (amino acids with hydrophobic side chain)
- Phe, Tyr, Trp (amino acids with hydrophobic side chain)
- Arg, His, Lys (amino acids with positively charged side chain)
- Ala, Gly (amino acids with small side chain)
- Ser, Thr (amino acids with uncharged side chains)
- Asn, Gln (amino acids with uncharged side chains)
- Asp, Glu (amino acids with negative charged side chain)

Generally, a conservative amino acid substitution refers to an amino acid substitution that does not alter the relative charge or size characteristics of the protein in which the amino acid substitution is made, and thus seldom alter the three-dimensional structure of the protein, which is why the biological activity are neither altered significantly.

The skilled person will thus acknowledge that a DNA polymerase such as an isolated large fragment DNA polymerase comprising an amino acid sequence according to SEQ ID No. 1 or SEQ ID No. 2, wherein the amino acid in position 449 is selected from the group consisting of Ser, Ala, Gly, Val, Leu, Ile and/or the amino acid in position 450 is selected from the group consisting to Ala, Gly, Val, Leu, Ile, Asp, Glu, Asn, Gln, and/or wherein the amino acid in position 451 is selected from the group consisting of Phe, Ala, Gly, Val, Leu, Ile, and/or wherein the amino acid in position 521 is selected from Arg, Ala, Gly, Val, Leu, Ile, provided that the amino acids in position 449 (S449), 450 (A450), 451 (F451) and 521 (R521) is not Ser, Ala, Phe and Arg, respectively, may have the same or approximately the same polymerase activity and strand displacement activity as a DNA polymerase according to SEQ ID NO. 3-8.

Also, the skilled person will understand that one or more amino acids may be deleted, inserted or added without altering the activity of the DNA-polymerase.

It is thus to be understood that the present invention encompasses DNA polymerases as disclosed in the appended claims, wherein such modifications as described above (substitutions, deletions, insertions and additions of amino acids) may be introduced without essentially altering the activity of the polymerase, i.e. in respect of polymerase activity and strand displacement activity.

Also, the skilled person will understand that Large Fragment DNA Polymerase I, is a DNA polymerase enzyme that lacks the 5' to 3' exonuclease activity of intact DNA Polymerase I, but does exhibit the 5' to 3' DNA polymerase and 3' to 5' exonuclease activities. An example of a well-known large fragment DNA polymerase I is the Klenow fragment.

According to yet another aspect, the present invention provides a DNA-polymerase or an enzymatically active fragment thereof comprising an amino acid sequence selected from the group consisting of SEQ ID No. 3, 4, 5, 6, 7, and 8, or comprising an amino acid sequence which is at least 60% sequence identical over the entire length of the sequence with SEQ ID No. 3, 4, 5, 6, 7, and 8, respectively.

According to another aspect, a DNA polymerase is provided comprising an amino acid sequence having at least 60%, such as at least 70%, such as at least 75%, such as at least 80%, such as at least 85% such as at least 90%, such as at least 95%, such as at least 97%, such as at least 98% or 99% sequence identity over the entire length of the sequence with an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, and SEQ ID No. 8.

Furthermore, the present invention also provides a nucleic acid molecule encoding an isolated DNA polymerase or an enzymatically active fragment thereof according to the present invention. According to one aspect, a nucleic acid molecule is provided comprising a nucleic acid molecule encoding an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, and SEQ ID No. 8 or comprising an amino acid sequence which is at least 60% sequence identical over the entire length of the sequence with SEQ ID No. 3, SEQ ID No. 4, SEQ ID No. 5, SEQ ID No. 6, SEQ ID No. 7, and SEQ ID No. 8, respectively.

According to yet another aspect, a nucleic acid molecule is provided comprising the sequence as depicted in SEQ ID No. 9 or nucleic acid molecules which is at least 80% sequence identical over the entire length of the sequence with SEQ ID No. 9, such as at least 85%, such as at least 90%, such as at least 95%, such as at least 97%, such as at least 98%, such as at least 99% sequence identical over the entire length of the sequence with SEQ ID No. 9.

Also, the skilled person will understand that one or more amino acids may be deleted, inserted or added without altering the activity of the enzyme of the present invention.

It is thus to be understood that the present invention encompasses DNA polymerases as disclosed in the appended claims, wherein such modifications as described above (substitutions, deletions, insertions and additions of amino acids) may be introduced without essentially altering the activity of the enzyme As used herein, both in respect of proteins and nucleic acid molecules or fragment thereof, when referring to "sequence identity", a sequence having at least x % identity to a second sequence means that x % represents the number of amino acids in the first sequence which are identical to their matched amino acids of the second sequence when both sequences are optimally aligned via a global alignment, relative to the total length of the second amino acid sequence. Both sequences are optimally aligned when x is maximum. The alignment and the determination of the percentage of identity may be carried out manually or automatically. Whenever referring to sequence identity herein, it is to be understood that the comparison is made with the entire sequence depicted in SEQ ID NO. 1-SEQ ID No. 9, respectively.

The skilled person will acknowledge that alignment for purposes of determining percent amino acid sequence identity can be achieved in various ways that are within the skill in the art, for instance, using publicly available computer software such as ClustalOmega (Sievers F, Higgins D G (2018) *Protein Sci* 27:135-145), Clustal W (Thomson et al., 1994, Nucleic Acid Res., 22, pp 4673-4680), Protein BLAST (from National Center for Biotechnology Information (NCBI), USA) or commercially available software such as Megalign (DNASTAR) software. Those skilled in the art can determine appropriate parameters for measuring alignment, including any algorithms needed to achieve maximal alignment over the full length of the sequences being compared. NCBI BLAST is another example of software used to determine amino acid sequence identity (MacWilliam et al., *Nucleic Acids Res.* 2013 July; 41(Web Server issue): W597-W600).

The skilled person will acknowledge that modifications may be introduced in a nucleic acid molecule which does not alter the amino acid sequence, e.g. the substitution of a nucleotide resulting in that the triplet affected by the substitution still codes for the same amino acid. For example, the amino acid isoleucine is encoded by the triplets (DNA codons) ATT, ATC, and ATA. Following, a substitution in the third nucleotide in the isoleucine triplet ATT from T to C or A, will not alter the resulting amino acid sequence. Such nucleotide modifications may be introduced by techniques well known to the skilled person (e.g. site directed mutagenesis) to adapt the nucleic acid sequence to the codons preferably used by a host cell and thus to enhance the expression of the enzyme.

Furthermore, nucleic acid molecules coding polypeptides which facilitates isolation and purification can be added to the nucleotide sequences of the present invention without affecting the activity of the resulting DNA polymerase.

Also, nucleic acid molecules coding signal peptide providing for secretion of the desired enzyme from a host cell may also be linked to the nucleic acid sequences of the present invention.

The present invention furthermore provides a composition comprising the DNA polymerase of the present invention or enzymatically active fragment thereof. The composition comprising an enzyme of the present invention may comprise buffers for optimised activity of the enzyme. The skilled person will acknowledge that buffers used in composition comprising an enzyme of the invention may vary and optimised according to the enzyme of choice and the process wherein the enzyme is used. The enzyme of the invention is retained within the conditions commonly used in molecular biology processes such as cloning processes, DNA assembly processes and DNA amplification processes well known to the skilled person, that is e.g. in respect of type and concentration of salt(s), pH conditions, etc. For example, well known buffers such as Tris buffer may be used, such as a Tris buffer having a pH above about 8.0, for example a pH within the range of 8.0 and 9.0. According to one aspect, the pH of the composition is within 8.5-9.0.

Furthermore, the skilled person will acknowledge that the type of salts and concentration thereof may vary. According to one aspect, the composition comprises one or more salts selected from the group consisting of NaCl and KCl. According to another aspect of the present composition comprises NaCl and KCl. According to yet another aspect, the composition comprises about 50 mM or more NaCl and about 50 mM or more KCl.

Preparation of the DNA Polymerase of the Present Invention

The DNA polymerase of the present invention and the enzymatically active fragments thereof or the nucleic acid molecule encoding them, is purified from or isolated from their natural environment or they are produced by recombinant DNA procedures well known to the skilled person.

Nucleic acid molecules encoding a DNA polymerase according to the present invention or encoding an enzymatically active fragment thereof may synthesized by methods well known to the skilled person or commercial suppliers well known to the skilled person, e.g. Genscript, Thermo Fisher Scientific etc.

The skilled person is well aware and familiar with the various available biotechnological techniques for expression of isolated or purified nucleic acid molecules for preparation of recombinant proteins by heterologous expression in various host cell systems using commonly available genetic engineering techniques and recombinant DNA expression systems, cf. e.g. "Recombinant Gene Expression Protocols, in Methods in Molecular Biology, 1997, Ed. Rocky S Tuan, Human Press (ISSN 1064-3745) or Sambrook et al., Molecular Cloning: A laboratory Manual (third edition), 2001, CSHL Press, (ISBN 978-087969577-4). For example, the nucleic acid molecule encoding the enzymes according to the present invention or encoding an enzymatically active fragment thereof may be inserted in a suitable expression vector comprising all the necessary transcriptional and translational regulatory sequences specifically adapted for directing the expression of the desired protein coding nucleic acid sequence in a suitable host cell. Suitable expression vectors are e.g. plasmids, cosmids, viruses or artificial yeast chromosomes (YAC's).

For example, DNA molecules to be expressed and used to prepare a DNA polymerase according to the present invention may be inserted into vectors used for propagation of the sequence of interest or for expression of the DNA polymerase encoding sequence of the invention. FastCloning is an example of an applicable method for this purpose.

According to one aspect of the invention, a vector, such as an expression vector is provided comprising the nucleic acid molecule encoding a DNA polymerase according to the present invention or an enzymatically active fragment thereof.

According to a further aspect, a vector, such as an expression vector is provided comprising a nucleic acid molecule encoding an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, and SEQ ID No. 8, or amino acid sequences having at least about 60% sequence identity over the entire length of the sequence such as at least, 70%, 75%, 80%, 85%, 90%, 95%, 96%, 97%, 98%, or 99% sequence identity over the entire length of the sequence of SEQ ID No. 1, SEQ ID No. 2, SEQ ID No. 3, SEQ ID No. 4, SEQ ID No. 5, SEQ ID No. 6, SEQ ID No. 7, and SEQ ID No. 8.

According to yet another aspect, a vector is provided comprising SEQ ID No. 9, or nucleic acid molecules which is at least 80% sequence identical over the entire length of the sequence with SEQ ID No. 9, or a sequence with 80% sequence identity over the entire length of the sequence of SEQ ID No. 9, such as at least, 85%, 90%, 95%, 96%, 97%, 98%, or 99% sequence identity over the entire length of the sequence of SEQ ID No. 9.

The skilled person will acknowledge that a DNA polymerase according to the present invention may be prepared using an expression vector comprising a nucleic acid molecule encoding a DNA polymerase according to the present invention, wherein said molecule is operably linked to a promotor adapted for the host cell in question.

The skilled person will furthermore acknowledge that a "promoter" as used herein refers to a region of DNA upstream (5'-prime) of a DNA coding sequence that controls and initiates transcription of the particular gene. The promoter controls recognition and binding of RNA polymerase and other proteins to initiate transcription. "Operably linked" refers to a functional linkage between a promoter and a second sequence, where the promoter sequence initiates and mediates transcription of the DNA sequence corresponding to the second sequence. In general, operably linked means that the nucleic acid sequences being linked are contiguous. For example, a vector adapted for expression of recombinant proteins in bacterial host cells may comprise a promotor applicable for bacterial expression systems, such as the T7 promoter.

A vector according to the present invention, may be isolated using standard plasmid isolation techniques well known to the skilled person, such as e.g. using a QIAprep™ Spin Miniprep kit from Qiagen™ or QIAGEN™ Plasmid Plus Maxi Kit.

Various commercially available host cells or viruses may be used. For example, bacterial host cells may be used, such as *E. coli*, BL21 cells or Rosetta 2 (DE3) cells (Novagen). Transformation of the expression vector may be performed by methods well known to the skilled person, e.g. using chemically competent cells.

Upon culturing the host cells in a suitable culturing media, the DNA polymerase of the present invention or an enzymatically active fragment thereof encoded by the expression vector in the host cell will be produced, and the resulting DNA polymerase may be collected and purified by methods well known to the skilled person.

The expression vector may furthermore include signal sequences for secretion of the expressed enzyme into the culture media.

As outlined above, the DNA polymerase of the present invention may be synthesized using recombinant DNA technology. Alternatively, the DNA polymerase of the present invention is prepared using cell-free expression systems, or it may be manufactured using chemical peptide synthesis methods, e.g. by stepwise condensation reaction of the carboxyl group of one amino acid to the amino group of another in accordance with the desired sequence of amino acids.

According to one aspect, a process for the preparation of a DNA polymerase of the present invention or a enzymatically active fragment thereof is provided, comprising the steps of (i) culturing a host cell comprising one or more expression vectors of the present invention suitable for the expression of the encoded DNA polymerase; and optionally (ii) isolating or obtaining the DNA polymerase from the host cell or from the culture medium (supernatant).

The skilled person will acknowledge that various methods are available for isolating and optionally purifying a recombinant expressed protein from a host cell or a culture medium. For isolation and purification of the obtained expressed DNA polymerase from the fermentation broth, one or more pre-treatments or clarification steps is commonly used first in order to remove large particles and biomass. Non-limiting examples of applicable pre-treatment steps are e.g. reverse osmosis, centrifugation, filtration methods and diafiltration, or a combination thereof. The obtained enzyme is then commonly purified by one or more of a variety of chromatographic methods well known to the skilled person, e.g. by affinity chromatography, ion-exchange chromatography, mixed-mode chromatography, hydrophobic interaction chromatography, size exclusion chromatography or other chromatography techniques, or a combination thereof.

For example, an enzyme expressed by a suitable host cell may be purified using an affinity chromatography method, such as using MabSelect™ SuRe™ media and a HiTrap MabSelect™ SuRe™ column mounted on an FPLC chromatography system, e.g. the BioRad NGC Discover™ 10 Pro system fitted with a 5 mm UV flow cell. After loading of the sample comprising the enzyme to be purified, the column is commonly washed one or more times with one or more applicable wash buffers, where after the protein is eluted using an applicable elution buffer. The obtained enzyme may be further purified using one or more of the chromatography methods listed above.

Use of the DNA Polymerase of the Invention

The present enzyme may be used in any molecular biology process where DNA polymerases are utilized. In particular, the DNA polymerase may be used in DNA amplification methods and DNA assembly processes, in particular multiple DNA assembly processes. The DNA polymerase is particular advantageous to use in molecular biology processes carried out at room temperature. Furthermore, the DNA polymerase of the invention is also useful in molecular biology processes where inactivation steps are preferably avoided.

Various methods based on homolog recombination techniques are known for assembly nucleic acid molecules. The present DNA polymerase is particularly useful in methods for assembly of nucleic acid molecules based on homologue recombination, and methods adapted for assembly of a large number of nucleic acid molecules. For example, the present DNA polymerase may be used in DNA assembly process as disclosed in EP1915446B1 or in in vitro recombination methods like the one disclosed in EP1929012B1.

In order to assembly multiple DNA molecules in the desired order, the ends to be assembled should share sequence identity ensuring that the respective overhangs of in question resulting from the exonuclease digestion step anneals (hybridize). The length of the overhang is preferably of a length sufficient to hybridize specifically to complementary overhangs of the shared region of sequence identity, so as to allow hybridization of the single-stranded overhangs. As illustration of the principles of annealing multiple dsDNA molecules, reference is made to FIG. 2 page 54 in SLIC: a method for sequence and ligation independent cloning by Li and Elledge, 2012, Gene Synthesis, pp 51-59.

The DNA polymerase of the present invention is particularly suitable due to that polymerization process can be carried out at room temperature. Furthermore, as the DNA polymerase of the present invention is heat labile, and inactivated at temperatures above about 25° C., resulting in that the polymerization process is easily ceased without the use of laborious inactivation steps. The fact that the present DNA polymerase exert a proof-reading activity in the form of a 3'-5' exonuclease makes it applicable in high fidelity amplification processes.

The DNA polymerase of the present invention having impaired or that lack strand displacement activity is in particularly useful in multiple DNA assembly processes.

Further the DNA polymerase of the present invention is a large fragment DNA polymerase lacking 5'-3' exonuclease domain and having impaired or lacking strand displacement activity is also particularly useful in multiple DNA assembly processes.

EXAMPLES

Example 1: Identification of the DNA Polymerase (MG Pol I) and Modification Thereof by Site-Directed Mutagenesis Upon analysis of a metagenome library originating from samples provided in Arctic area around Svalbard, a DNA sequence encoding a polymerase according to SEQ ID No. 2 was identified.

The vector pET151/D-TOPO® containing the codon-optimized gene encoding the large fragment of the identified DNA polymerase (SEQ ID No. 9) was purchased from the Invitrogen GeneArt Gene Synthesis service from Thermo Fisher Scientific.

In order to provide modified enzymes, wherein the strand displacement activity of the identified enzyme is reduced, impaired or inactivated compared with the wild type enzyme various mutations were introduced in SEQ ID No. 9 using the QuikChange II Site-Directed Mutagenesis Kit (Agilent Technologies). The introduced modification was confirmed by sequencing analysis.

Example 2: Preparation of Recombinant DNA Polymerase I (MG Pol I) of the Invention Recombinant protein production of MG Pol I large fragment and its mutants was performed in Rosetta 2 (DE3) cells (Novagen®). The cells grew in Terrific Broth media/ampicillin (100 μg/ml) and gene expression was induced at $OD_{600\ nm}$ 1.0 by addition of 0.1 mM IPTG. Protein production was carried out at 15° C. overnight. For protein purification the pellet of a ½-l cultivation was resuspended in 50 mM HEPES pH 7.5 (at 25° C.), 500 mM NaCl, 5% glycerol, 1 mM DTT, pH 7.5, 0.15 mg/ml lysozyme, 1 protease inhibitor tablet (Complete™, Mini, EDTA-free Protease Inhibitor Cocktail, Roche) and incubated on ice for 30 min. Cell disruption was performed by sonication with the VCX 750 from Sonics® (pulse 1.0/1.0, 15 min, amplitude 25%). In the first step, the soluble part of the $His_6$-tagged protein present after centrifugation (48384 g, 45 min, 4° C.) and filtration (Ø 0.45 μm) was purified by immobilized $Ni^{2+}$-affinity chromatography. After a wash step with 50 mM HEPES, 500 mM NaCl, 35 mM imidazole, 5% glycerol, 1 mM DTT, pH 7.5 the protein was eluted at an imidazole concentration of 250 mM and further transferred into 50 mM HEPES, 500 mM NaCl, 10 mM $MgCl_2$, 5% glycerol, pH 7.5 by use of a desalting column. The second step was the cleavage of the tag by the TEV protease performed over night at 4° C. in 50 mM Tris pH 8.0, 0.5 mM EDTA and 1 mM DTT. To separate the protein from the $His_6$-tag and the $His_6$-tagged TEV protease a second $Ni^{2+}$-affinity chromatography has been performed in the third step by applying 50 mM HEPES, 500 mM NaCl, 5% glycerol, 1 mM DTT, pH 7.5. The final protein solution was concentrated and stored with 50% glycerol at −20° C. for activity assays.

Example 3: Measuring of Polymerase Activity of the Present Enzyme

In order to measure the polymerase activity of the present enzyme and also compare said novel enzyme with known DNA polymerases, an assay based on a molecular beacon probe (modified from Summerer, *Methods Mol. Biol.,* 2008, 429, 225-235) was used. The molecular beacon template consists of a 23 mer loop that is connected by a GC-rich 8 mer stem region (sequence is indicated in italics) and a 43 mer extension. Due to the loop formation the fluorophores Dabcyl and FAM are in close proximity and thus quenched. Upon extension by the DNA polymerase I of the primer that is annealed to the molecular beacon template the stem is opened and the increase in distance of the two fluorophores is measured by the restoration of FAM fluorescence (excitation 485 nm, emission 518 nm).

molecular beacon template (SEQ ID. No. 10)

5'-*GGCCCGT*$^{Dabcyl}$AGGAGGAAAGGACATCTTCTAGCA*T*$^{FAM}$*ACGGGC*

*C*GTCA-AGTTCATGGCCAGTCAAGTCGTCAGAAATTTCGCACCAC-3' primer (SEQ ID. No. 11)

5'-GTGGTGCGAAATTTCTGAC-3'

The molecular beacon substrate was produced by incubating 20 μl of 10 μM molecular beacon template and 15 μM primer in 10 mM Tris-HCl pH 8.0, 100 mM NaCl for 5 min at 95° C. The reaction was then let to cool down at room temperature for 2 h. The substrate solution was stored at −20° C. with a final concentration of 10 μM.

Fifty microliter reactions consisted of 200 nM substrate and 200 μM dNTP (equimolar amounts of dATP, dGTP, dCTP and dTTP). The reaction further contained 5 mM $MgCl_2$ in 50 mM Tris-HCl pH 8.5, 100 mM KCl, 1 mM DTT, 0.2 mg/ml BSA and 2% glycerol. The activity assay was carried out at 25° C. in black 96-well fluorescence assay plates (Corning©). The reaction was initiated by addition of protein solution, i.e. MG pol I and its variants. The increase in FAM fluorescence was measured as relative fluorescence units in appropriate time intervals by exciting at 485 nm and emission at 518 nm. The measurement was performed in a SpectraMax® Gemini Microplate Reader (Molecular Devices).

The results are shown in FIG. 3 and shows that the enzyme of the present invention has a high DNA polymerase activity.

Example 4: Strand Displacement Activity Assay

The assay is based on an increase in fluorescence signal that is measured upon displacement of the quenched reporter strand. This is only achievable through strand-displacement activity of the DNA polymerase.

The substrate for the strand-displacement activity assay consists of a "cold" primer of 19 oligonucleotides and a reporter strand consisting of 20 oligonucleotides that is labeled with the TAMRA fluorophore [TAMRA] at its 3' end. The template strand consists of 40 oligonucleotides and is labeled with the Black Hole Quencher 2 (BHQ2) at its 5' end. The primers are annealed to the template strand leaving a one-nucleotide gap at position 20 on the template strand. Furthermore, are the labels in close proximity and thus the fluorophore TAMRA is quenched by BHQ2. Upon strand-displacement activity of the DNA polymerase I the TAMRA labeled oligonucleotide is displaced from the template strand. As a consequence, the fluorophore and the quencher are no longer in close proximity and an increase in TAMRA fluorescence can be measured (excitation 525 nm, emission 598 nm).

```
                                      (SEQ ID No. 12)
5'-TATCCACCAATACTACCCTCGATACTTTGTCCACTCAAT

[TAMRA]-3'

                                      (SEQ ID No. 13)
3'-ATAGGTGGTTATGATGGGATGCTATGAAACAGGTGAGTT

A[BHQ2]-5'
```

The strand-displacement activity of the DNA polymerase of the present invention and its variants expressed as mRFU/min/μg has been analyzed using the above-described strand-displacement activity assay.

The substrate for the strand-displacement activity assay was produced by incubating 20 μl of 10 μM "cold" primer, 10 μM reporter strand and 10 μM template strand in 10 mM Tris-HCl pH 8.0, 100 mM NaCl at 95° C. for 5 min. The reaction was then let to cool down at room temperature for 2 h. The substrate solution was stored at −20° C. with a final concentration of 10 μM.

Fifty microliter reactions consisted of 200 nM substrate and 200 μM dNTP (equimolar amounts of dATP, dGTP, dCTP and dTTP). The reaction further contained 5 mM $MgCl_2$ in 50 mM Tris-HCl pH 8.5, 100 mM KCl, 1 mM DTT, 0.2 mg/ml BSA and 2% glycerol. The activity assay was carried out at 25° C. in black 96-well fluorescence assay plates (Corning©). The reaction was initiated by addition of protein solution, i.e. MG pol I and its variants. The increase in TAMRA fluorescence was measured as relative fluorescence units in appropriate time intervals by exciting at 525 nm and recording emission at 598 nm. The measurement was performed in a SpectraMax® M2$^e$ Microplate Reader (Molecular Devices).

Figure 5:
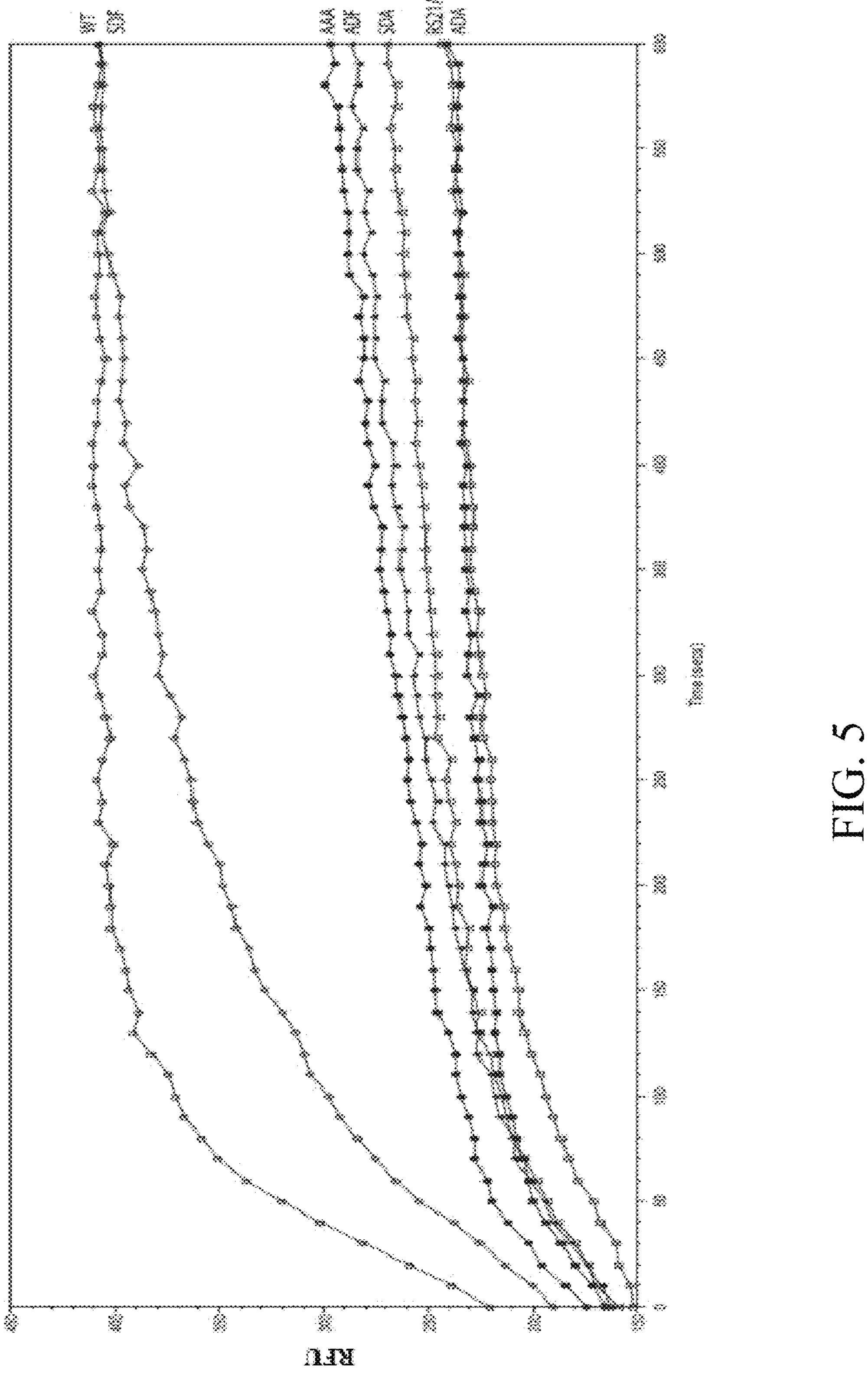
FIG. 5 shows a comparison of the polymerase activity of the large fragment DNA polymerases of the present invention at 25° C., represented by the wild type (wt) DNA polymerase, the A450D-mutant (SDF), S449A+F451A-mutant (AAA), S449A+A450D-mutant (ADF), the A450D+F451A-mutant (SDA), the S449A+A450D+F451A-mutant (ADA) and the R521A-mutant.

The results of the analysis are shown in FIGS. 5 and 6.

OVERVIEW OF THE SEQUENCE NUMBERS REFERRED TO IN THE SPECIFICATION AND SEQUENCE LISTING

| SEQ ID No. | Sequence information |
|---|---|
| 1 | Large fragment DNA polymerase I with variable amino acid positions 449, 450, 451 and 521 |
| 2 | Wild type sequence of large fragment DNA polymerase I of marine origin identified by metagenomic analysis |
| 3 | DNA polymerase wherein alanine in position 450 is replace by aspartate compared with the wild type sequence SEQ ID No. 2 (A450D SDF) |
| 4 | DNA polymerase wherein serine in position 449 and phenylalanine in position 451 is replace by alanine compared with the wild type sequence SEQ ID No. 2 (S449A/F451A, AAA) |
| 5 | DNA polymerase wherein serine in position 449 and alanine in 450 is replace by alanine and aspartate, respectively, compared with the wild type sequence SEQ ID No. 2 (S449A/A450D, ADF) |
| 6 | DNA polymerase wherein alanine in position 450 and phenylalanine in position 451 is replaced by aspartate and alanine, respectively compared with the wild type sequence SEQ ID No. 2 (A450D/F451A, SDA). |
| 7 | DNA polymerase wherein serine in position 449 and alanine in position 450 and phenylalanine in position 451 is replace by alanine, aspartate and alanine, respectively compared with the wild type sequence SEQ ID No. 2 (S449A/A450D/D451A, ADA) |
| 8 | DNA polymerase wherein arginine in position 521 is replaced by alanine compared with the wild type sequence SEQ ID No. 2 (R521A) |
| 9 | Nucleic acid sequence encoding a DNA polymerase comprising an amino acid sequence according to SEQ ID No. 2 and codon optimized |
| 10 | molecular beacon template used in polymerase activity experiment |
| 11 | primer used in polymerase activity experiment |
| 12 | Sequence used in strand displacement activity experiment |
| 13 | Sequence used in strand displacement activity experiment |

The invention claimed is:

1. An isolated DNA polymerase, wherein said DNA polymerase is the amino acid sequence selected from the group consisting of SEQ ID NOs: 3, 4, 5, 6, 7, and 8, or is at least 98% identical to the amino acid sequence selected from the group consisting of SEQ ID NOs: 3, 4, 5, 6, 7, and 8, wherein the amino acid in position 450 of SEQ ID NO: 3 is Asp, the amino acids in positions 449 and 451 of SEQ ID NO: 4 are Ala, the amino acids in positions 449 and 450 of SEQ ID NO: 5 are Ala and Asp, respectively, the amino acids in positions 450 and 451 of SEQ ID NO: 6 are Asp and Ala, respectively, the amino acids in positions 449, 450 and 451 of SEQ ID NO: 7 are Ala, Asp and Ala, respectively, and the amino acid in position 521 of SEQ ID NO: 8 is Ala wherein the DNA polymerase which is at least 98% identical to the amino acid sequence selected from the group consisting of SEQ ID NOs: 3 4, 5, 6, 7 and 8 only contains conservative amino acid substitutions; and wherein said DNA polymerase has no strand displacement activity.

2. The isolated DNA polymerase according to claim 1, wherein the DNA polymerase lacks 5'-3' exonuclease activity.

3. The isolated DNA polymerase according to claim 1, wherein said DNA polymerase is at least 99% identical to the amino acid sequence selected from the group consisting of SEQ ID NOs. 3, 4, 5, 6, 7, and 8.

4. The isolated DNA polymerase according to claim 1, wherein said DNA polymerase is the amino acid sequence selected from the group consisting of SEQ ID NOs. 3, 4, 5, 6, 7, and 8.

5. A composition comprising the isolated DNA polymerase of claim 1 and a buffer.

6. A method for assembly of two or more double stranded (ds) DNA molecules, said process comprising the steps of:

(a) providing two or more dsDNA molecules, wherein each of the dsDNA molecules comprises a single stranded DNA overhang, wherein the terminal end of the DNA overhang of each of the two or more dsDNA molecules comprises a complementary sequence such that the two or more dsDNA molecules are able to hybridize to each other and form annealed molecules; and (b) incubating the two or more dsDNA molecules under conditions for annealing said two or more dsDNA molecules;

(c) contacting the annealed molecules with the DNA polymerase of claim 1 and filling in gaps of the annealed molecules.

7. A method for performing a nucleotide polymerization reaction, said method comprising the steps of:

(a) providing a reaction mixture comprising the DNA polymerase of claim 1, a template nucleic acid molecule, an oligonucleotide primer which is capable of annealing to a portion of the template nucleic acid molecule, and one or more nucleotides; and (b) incubating said reaction mixture under conditions for annealing the oligonucleotide primer to the template nucleic acid molecule and extending said oligonucleotide primer annealed to the template nucleic acid molecule using said DNA polymerase.

8. A method of amplifying a nucleic acid said method comprising the steps of:

(a) providing a reaction mixture comprising the DNA polymerase of claim 1, a template nucleic acid molecule, an oligonucleotide primer which is capable of annealing to a portion of the template nucleic acid molecule, and nucleotides; and (b) generating a polynucleotide by incubating said reaction mixture under conditions for annealing the oligonucleotide primer to the template nucleic acid molecule and extending said oligonucleotide primer annealed to the template nucleic acid molecule using said DNA polymerase.

* * * * *